United States Patent [19]
Groger et al.

[11] Patent Number: 5,766,956
[45] Date of Patent: Jun. 16, 1998

[54] DIODE LASER-BASED CHEMICAL AND BIOLOGICAL SENSOR

[75] Inventors: Howard P. Groger, Gainesville, Fla.; Russell J. Churchill, Radford, Va.; Shu-Fang Luo; K. Peter Lo, both of Blacksburg, Va.

[73] Assignee: American Research Corporation, Radford, Va.

[21] Appl. No.: 862,929

[22] Filed: May 27, 1997

[51] Int. Cl.$^6$ ................................................. G01N 21/63
[52] U.S. Cl. .................. 436/164; 436/172; 422/82.05; 422/82.08; 422/82.11; 356/318
[58] Field of Search ................ 422/82.05, 82.08, 422/82.07, 82.09, 82.11; 356/318; 436/164, 172, 524–527

[56] References Cited

U.S. PATENT DOCUMENTS

| | | |
|---|---|---|
| 4,894,833 | 1/1990 | Carlin . |
| 5,107,316 | 4/1992 | Jelley et al. ............... 357/25 |
| 5,109,386 | 4/1992 | Bradley . |
| 5,177,758 | 1/1993 | Oka et al. . |
| 5,208,878 | 5/1993 | Thulke . |
| 5,317,897 | 6/1994 | Jelley et al. ............... 73/31.06 |
| 5,439,647 | 8/1995 | Saini . |
| 5,491,712 | 2/1996 | Lin et al. . |
| 5,492,840 | 2/1996 | Malmqvist et al. . |
| 5,591,407 | 1/1997 | Groger et al. ............ 422/82.05 |

*Primary Examiner*—Jeffrey Snay
*Attorney, Agent, or Firm*—James Creighton Wray; Meera P. Narasimhan

[57] ABSTRACT

A-compact, diode laser-based sensor has applications in biological and chemical analysis. Unlike existing optical waveguide-based sensors, no external coupling to external optical fibers or waveguides is required to perform optical chemical, immunological or nucleic acid-based assay or to detect the presence of toxic or otherwise important chemicals. The sensor includes a surface-sensitive diode laser having a substrate layer, an n-contact layer positioned on a bottom surface of the substrate, an n-clad layer overlying the top surface of the substrate, a first guide layer overlying the n-clad layer, a quantum well layer overlying the first guide layer, a second guide layer overlying the first quantum well layer, a p-clad layer overlying the second guided layer and a p-doped cap layer overlying the p-clad layer. A pair of electrodes separated by a surface-sensitive region is positioned on the cap layer. The surface active region includes an oxide layer grown on the thick cap layer and an absorbing or non-absorbing film deposited on the oxide layer. For internal reflection, inorganic material coatings are applied to end facets or Bragg reflectors are etched in the cap layer. Detectors are positioned proximate the diode laser for detecting changes in film thickness or refractive index, absorption or other optical properties resulting from film deposition, surface reactions such as immunological or ion-exchange reactions, or other detectable processes.

33 Claims, 5 Drawing Sheets

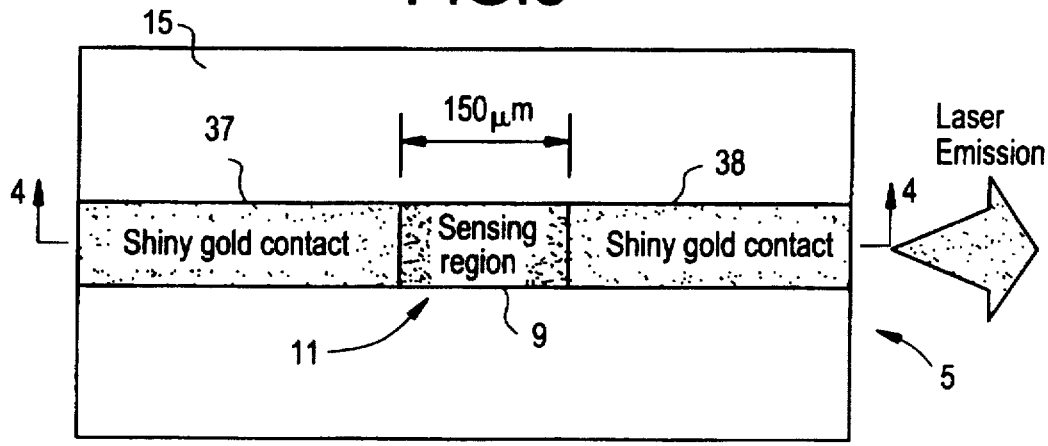
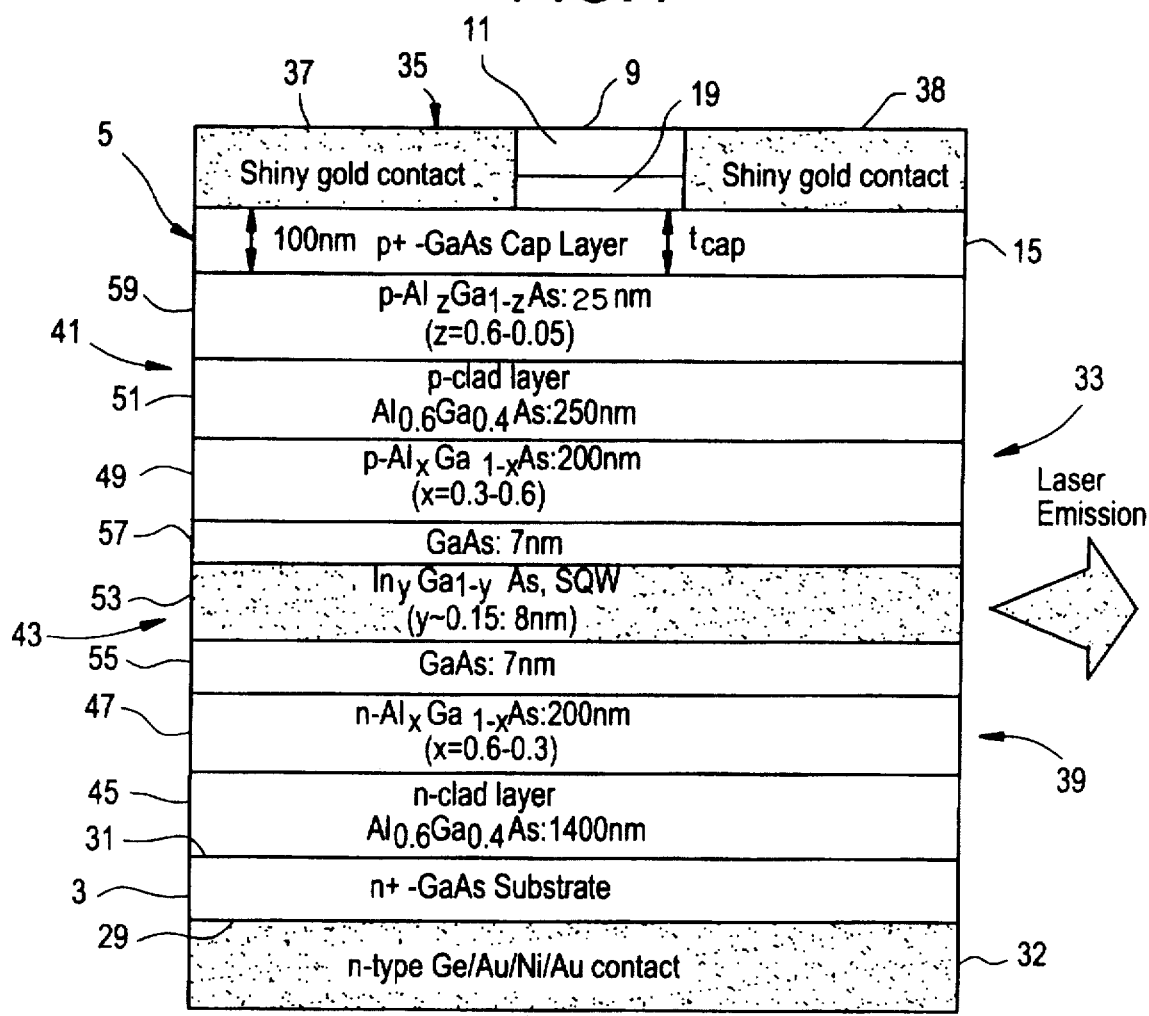

Dye 1 in Acetone

Dye 2 in Acetone in Ethanol

DIODE LASER-BASED CHEMICAL AND BIOLOGICAL SENSOR

BACKGROUND OF THE INVENTION

The present invention relates to instrumentation for rapid identification and detection of vapors, chemical constituents, biological materials, micro-organisms and toxins.

Currently, considerable effort is being expended to develop simple, rapid, low-cost methods and apparatus for monitoring micro-organisms and toxins considered for use in biological warfare and in terrorist activities. Current optical instruments employing both immunological and nucleic acid-based methods offer the capability of monitoring micro-organism and toxic concentrations down to picomolar levels ($10^{-12}M$). Existing optical fiber immunoassay systems are competitive with light-addressed, potentiometric sensor (LAPS) technology in that the speed of response and sensitivity are similar for those two approaches when used in immunoassay. The LAPS system has increased sensitivity in nucleic acid evaluation. Another existing system, the ORIGEN system, provides considerably higher sensitivity at the expense of increased detection times. Each of those existing systems and methods has disadvantages in terms of sensitivity, reproducibility and speed of response. Needs exist for sensitive, low-cost optical instruments which can detect trace levels of gases and volatiles, biological compounds and biochemical materials in solution or in air.

Biosensing is an emerging technology that has been shown to have practical applications in fields such as clinical diagnostics, environmental monitoring and process control. In a biosensor, biological molecules provide the recognition of a substance to be detected. Existing biosensors are based on antibody-antigen, receptor-ligand, carbohydrate-lectin or nucleic acid-analyte methods in which the selective response between immobilized probe molecules and analytes present in solution is detected using electrochemical, optical, thermal or acoustic monitoring techniques. Optical techniques involve the use of luminescence, changes in optical absorption, surface plasmon effects or optically generated electrochemical effects to monitor the presence of the analyte. In many existing sensing techniques, the sensitivity of the sensor is increased by detecting the interaction between the probe material and the analyte within the evanescent field of an optical waveguide. For absorption or fluorescence-based evanescent wave sensing, a recognition event is transduced as a change in transmission through the waveguide or in fluorescence intensity. For immunoassay, both competitive and noncompetitive protocols can be used. In a competitive protocol, capture antibodies are covalently coupled to a silanized optical surface using heterobifunctional molecules, such as N-gamma-maleimidobutyryloxy succinimide ester. The capture antibody provides a selective surface for deposition of the labeled antigen. The removal of the labeled antigen under competition with the analyte antigen takes place within the evanescent field of a fiber-optic waveguide. In a noncompetitive sandwich assay, the capture antibody is used to bond analyte antigen to the sensor surface. The labeled antibody is then used to detect the presence of bound antigen at the sensor surface by affecting the optical characteristics of the waveguide structure.

Generally, in biological assays employing lasers, light is coupled from the laser to an optical fiber or waveguide structure on which the probe material is immobilized at either the distal end or along the optical path traversed by light in the waveguide. Sensors based on immobilization of the probe material along the waveguide provide considerably higher sensitivity as a result of the longer optical interaction length and reduction of interferences resulting from light scattered from the propagating laser beam. The sensitivities of immunological and nucleic acid-based biological assays performed using existing laser-based sensors are limited by the precision of measurements made in the absence of analyte molecules. That precision is, in turn, related to the selectivity of the ligand binding event, the occurrence of non-specific bonding and interference caused by absorption or fluorescence of unbound molecules in solution. The precision of optical waveguide based biological assay is also dependent on the accuracy of achieving repeatable optical coupling between the laser source and the optical fiber or waveguide-based sensor. The lack of precision, unpredictability and low sensitivity encountered using existing lasers in biological assay have rendered existing sensors and sensing methods inadequate.

To develop biosensors exhibiting rapid response to micro-organisms and biological toxins, suitable absorbent or fluorescent materials must be selected to serve as labels. Most labeling materials that can be bonded to biomolecules or supporting matrices in biochemical sensors require light sources that operate in the UV/Visible regions. Those light sources are extremely expensive and have physical dimensions that prohibit incorporation into a lightweight sensor system. The far-visible and the near-IR spectral regions (600–1,000 nm) are the areas of low interference, where only a few classes of molecules exhibit significant absorption and fluorescence. Results from existing optical waveguide-based immunoassay systems suggest that background fluorescence can be reduced by a factor of 20 by increasing the wavelength of the excitation source from 490 nm to 650 nm. Needs exist for lightweight, compact biosensors having light sources that are compatible for use with near-IR labels.

SUMMARY OF THE INVENTION

The present invention is a compact, diode laser-based sensor having applications in the fields of chemical and biological analysis. The present sensor has advantages over existing optical waveguide-based methods and apparatus in that no optical coupling to external optical fibers or waveguides is required to perform optical chemical, immunological or nucleic acid based assay or to detect the presence of toxins or otherwise important chemicals. The compact sensor has immediate uses in environmental monitoring, biological threat assessment, treaty verification and detoxification processes.

The present sensor uses a surface-sensitive diode laser to detect changes in film thickness, refractive index, absorption or other optical properties resulting from film deposition, immunological (antibody-antigen) reaction, metachromasy, hydrogen biding, ion exchange or other detectable process. A polymer film including absorbing dyes or non-absorbing materials is coupled to the surface of the laser. The response of the surface-sensitive diode laser to coupling of capture antibodies and antigen, deposition of thin films or other activity at the laser surface is monitored using optical power measurements or spectral measurements. The present sensor can be used for both homogenous and heterogeneous immunoassay as well as other biochemical modes of analysis. In particular, inclusion of the surface-sensitive diode laser in the sensor allows the sensor to monitor thin film deposition reactions, an application currently achievable using surface plasmon resonance technology. The surface-sensitive diode laser exhibits signal repeatability when power-current characteristics are evaluated. Improved signal reproducibility is provided when spectral techniques are used to monitor the laser's output characteristics. For improved sensor reliability, a surface-sensitive diode laser capable of distributed feedback is provided.

The present apparatus and method of detection are based on a sensor design involving a surface-sensitive diode laser structure grown on a substrate. The diode laser responds directly to the presence of an analyte, thereby eliminating the need for optical alignment or optical coupling. The present sensor is biased at a level where the presence of the analyte alters the lasing action of the diode laser. That allows for increased sensitivity over existing optical fiber immunoassay procedures. By using evanescent wave excitation, the present sensor restricts the recognition event to a fraction of a wavelength away from the surface of the waveguide, an important advantage in immunoassay applications. The surface-sensitive diode laser for use in the present sensor is capable of monitoring the deposition of dielectric films as thin as 1.2 nm and can be used to detect changes in film thickness, refractive index and absorption. The repeatability of measurements performed using the surface-sensitive diode laser provides for a biosensor with a modular laser sensor head. The present diode laser-based sensor is significant in establishing low-cost biosensor technologies in defense, biomedical and environmental assay applications.

The present sensor includes a semiconductor diode laser having a surface-sensitive region for use as a substrate for immunological or nucleic acid probes. The response of the surface-sensitive diode laser to environmental changes in the surface sensitive region is monitored using optical power measurements and spectral measurements. Sensors using surface-sensitive diode lasers are capable of monitoring the deposition of thin absorptive films as well as films containing little or no absorptive material. The present invention has applications in both homogenous and heterogenous immunoassay as well as other biochemical modes of analysis.

The diode laser of the present sensor operates as an active optical waveguide for biological assay. The effects on sensor output of coupling between the diode laser and the probe materials immobilized on the surface of the laser are reduced to a negligible level because the waveguide is defined microlithographically on the diode laser surface.

The present sensor surpasses the capabilities of existing sensors by providing part-per-billion sensitivities.

The present invention has applications in the medical diagnostics and environmental microbial assay markets, in the area of environmental monitoring and process control and in the measurement of analytes of interest in industrial processing and quality control. The reduced cost and portability of the present sensor offers advantages in process inspection, in point-of-care medical diagnosis and in environmental site monitoring.

A surface-sensitive diode laser sensor includes a substrate having a bottom surface and a top surface. A contact layer is positioned on the bottom surface of the substrate. A surface-sensitive diode laser is grown on the top surface of the substrate. A detector is positioned proximate the diode laser or included in the internal structure of the diode laser. The diode laser further includes a lasing structure positioned on the top surface of the substrate and a cap layer positioned on the lasing structure. A segmented electrode is positioned on the cap layer. The segmented electrode includes a first electrode and a second electrode separated by a surface-sensitive region. The surface-sensitive region further includes a sensitive coating prepared on the thick cap layer in the surface-sensitive region.

The lasing structure of the diode laser includes a lower laser region positioned on the upper surface of the substrate, an upper laser region and a quantum well sandwiched between the upper laser region and the lower laser region. The lower laser region includes a n-cladding layer positioned on the upper surface of the substrate and an n-guide layer overlying the n-cladding layer. The upper laser region includes a p-guide layer positioned on the quantum well and a p-cladding layer overlying the p-guide layer. The cladding and guide layers are preferably aluminum gallium arsenide layers. The quantum well is a central layer sandwiched between a pair of undoped layers. The central layer is preferably a gallium indium arsenide well and the undoped layers are preferably gallium arsenide layers.

In preferred embodiments of the present sensor, a p-layer is positioned between the cap layer and the lasing structure.

Preferably, the cap layer is a gallium arsenide layer having p-conductivity. The first and second electrodes are gold electrodes and the first contact layer is a n-type Ge/Au/Ni contact layer. The substrate is a doped n-type gallium arsenide substrate.

End facets are defined by side edges of the substrate, contact layer, lasing structure, cap layer and segmented electrode. In preferred embodiments of the present sensor, an inorganic chemical coating is applied to the end facets for passivating the end facets.

For improved sensitivity, upper surfaces of the cap layer outside of the surface-sensitive region have etched surface corrugations defining a grating surface. The grating surface preferably includes Bragg grating reflectors.

In preferred embodiments of the present sensor, a coupling layer, such as an oxide layer, is positioned between the sensitive coating and the thick region of the cap layer. The sensitive coating applied to the oxide layer includes absorbing dyes or fluorescent dyes immobilized in a polymer or ceramic material. The dyes are preferably selected from the group including 4-(2-(2-chloro-3-((2,6 diphenyl-4H-thiopyran-4-ylidene)ethylidene)-1-cyclohexen-1-yl) ethenyl)-2,6 diphenylthiopyrylium tetrafluoroborate (Aldrich 40,512-4) in a Nafion binder, 1-Butyl-2-(2-(3-((1-butyl-6-clorobenz(cd)indol-2(1H)-ylidene)ethylidene)-2-chloro-1-cyclohexen-1-yl)ethenyl)-6-chlorobenz(cd) indolium tetrafluorborate (Aldrich 40,517-5) in a Nafion binder, 4-(2-(2-chloro-3-((2,6 diphenyl-4H-thiopyran-4-ylidene) ethylidene)-1-cyclohexen-1-yl)ethenyl)-2,6 diphenylthiopyrylium tetrafluoroborate (Aldrich 40,512-4) having an attached pendant isothiocyanato functional group, 1-Butyl-2(2-(3-((1-butyl-6-clorobenz(cd)indol-2(1H)-ylidene) ethylidene)-2-chloro-1-cyclohexen-1-yl)ethenyl)-6-chlorobenz(cd) indolium tetrafluoroborate (Aldrich 40,517-5) having an attached pendant isothiocyanato functional group, napthalocyanine dyes, and napthalocyanine dyes having Vanadium metal centers.

In other preferred embodiments of the present sensor, the sensitive coating includes non-absorbing materials. Possible non-absorbing materials include, but are not limited to, antibody materials and nucleic acid materials of a known sequence.

The detector of the present sensor is preferably a wavelength-sensitive detector for measuring an optical output of lasing structure. Possible wavelength-sensitive detectors for use in the present sensor include, but are not limited to grating-based spectrographs, Fizeau interferometers, Fourier transform interferometers or any other wavelength sensitive interferometer, and gratings in combination with array detectors, such as charged coupled device cameras or photodiode arrays.

The detector may also monitor changes in electrical characteristics such as output power-injection current characteristics. For those embodiments, the detector may include a pulse generator for developing pulse signals at a constant repetition rate and for delivering the pulse signals through a micropositioner to the lasing structure of the diode laser, a photodiode for receiving emitted laser signals from the lasing structure and for converting the laser signals to electrical signals, and gated electronics for comparing the electrical signals to the pulse signals from the pulse generator for detecting and identifying chemicals.

A monolithic optical sensor includes a substrate having a top surface and a bottom surface, first and second diode lasers grown on the top surface of the substrate, and a detector for detecting outputs from the lasers. The thickness of the cap layer of the first diode laser in the surface-sensitive region is optimal for surface sensitivity. A blocking layer may be applied to the surface sensitive region of the second diode laser, thereby rendering the second diode laser insensitive and useful as a reference. Preferably, upper surfaces of the cap layers of the diode laser outside of the surface-sensitive regions have surface corrugations. In preferred embodiments, the diode lasers each have a laser generation region positioned beneath the electrodes and a laser detection region positioned at a far end of the laser. The cap layer is discontinuous between the laser detection region and the laser generation region. A single electrode is positioned on the cap layer overlying the laser detection region.

Embodiments of the present sensor having multiple diode lasers with differing dyes immobilized in differing polymer matrices may be provided as means for detecting and identifying any chemical.

These and further and other objects and features of the invention are apparent in the disclosure, which includes the above and ongoing written specification, with the claims and the drawings.

BRIEF DESCRIPTION OF THE DRAWINGS

FIG. 3 is a top view of a preferred diode laser of the present sensor.

FIG. 4 is a cross-sectional view of the diode laser of FIG. 3 taken along A—A.

DETAILED DESCRIPTION OF THE PREFERRED EMBODIMENTS

Figure 1:
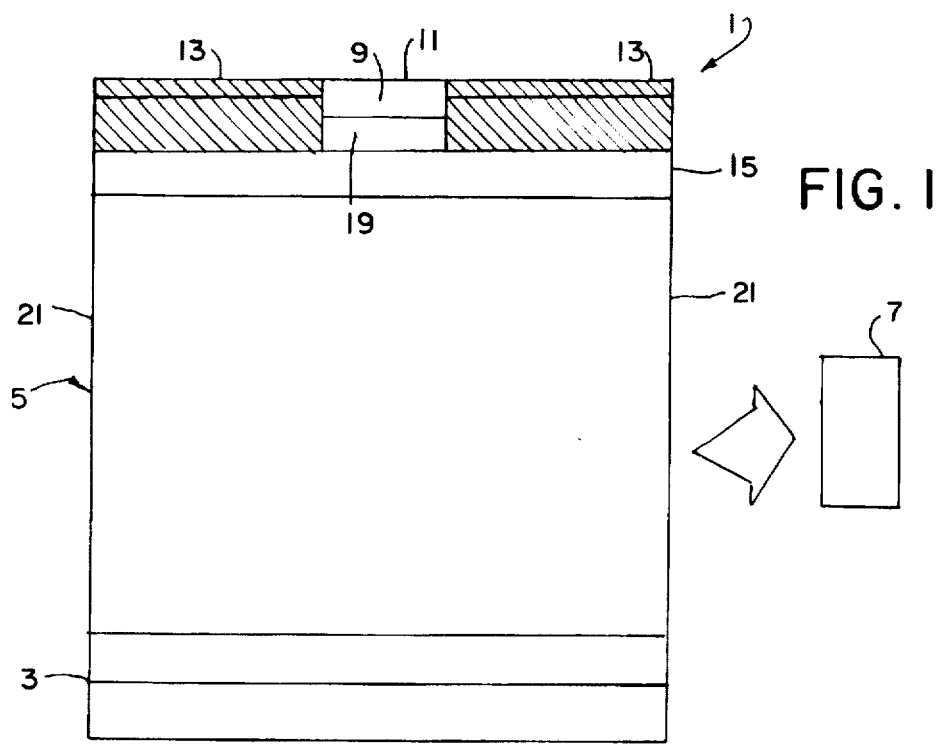
FIG. 1 is a schematic illustration of the present sensor.

As shown in FIG. 1, a diode laser-based biosensor 1 uses evanescent wave sensing techniques within a diode laser cavity. The present sensor 1 includes a substrate 3, a surface-sensitive diode laser 5 grown on the substrate 3 and a detector 7 positioned proximate or include as part of the diode laser 5. A responsive coating 9 is applied to the surface-sensitive region 11 of the diode laser 5. The diode laser-based sensor 1 can be operated directly or in conjunction with a flow cell to allow sample transport to the surface-sensitive region and to permit the use of sample regeneration procedures.

As shown in FIG. 1, electrodes 13 are positioned on the upper surface 15 of the diode laser 5. A surface-sensitive region 11 is formed between the electrodes 13. A responsive coating 9, such as a polymer film containing absorbing dyes or a non-absorbing film including immunological materials, is coupled to the upper surface 15 of the diode laser 5. Preferably, a bonding layer 19, such as an oxide layer, is situated between the responsive coating 9 and the upper surface 15 of the diode laser 5.

For improved sensitivity, the diode laser 5 may be passivated. In one preferred embodiment, the end facets 21 of the diode laser 5 are passivated using inorganic material coatings. In another preferred embodiment, the cap layer 15 of the diode laser 5 is passivated through the deposition of organic or inorganic films at the laser surface.

Figure 2:
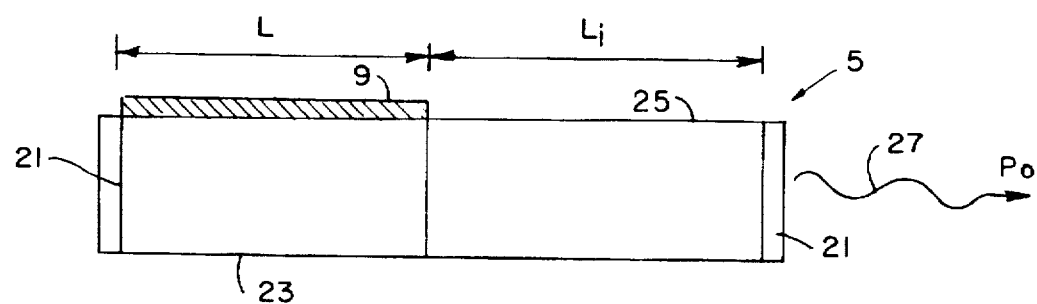
FIG. 2 schematically shows a surface-sensitive diode laser for use in the present sensor.

FIG. 2 schematically shows a surface-sensitive diode laser 5 for use in the present sensor 1. The laser 5 includes an unpumped region 23 on which the label coating 9 is deposited and a protected pumped region 25 having little or no interaction with the environment. The lengths of the pumped region 25 and the unpumped region 23 are $L_i$ and $L$, respectively, and their mode loss coefficients are represented by $\alpha_i$ and $\alpha$, respectively. The output power 27 of the laser 5, $P_o$, is a function of the absorption losses of an absorbing or fluorescent dye in the vicinity of the cladding layer of the diode laser 5.

The inclusion of a surface-sensitive diode laser 5 in the present sensor 1 allows changes in the evanescent field of the surface-sensitive region 11 to provide larger effects on the laser optical power-current characteristics. The diode laser 5 preferably includes a current-pumped region 25 with a conventional thin p-clad design in conjunction with a surface-sensitive section ii. The diode laser 5 is operable at reasonable driving currents and exhibits repeatable power-current characteristics. Preferably, the diode laser 5 has a thin p-clad current driving region 25. Diode lasers 5 having that geometry are readily fabricated using existing laser processing technology and exhibit considerable sensitivity to changes in the absorption of materials deposited on the laser surface.

FIGS. 3 and 4 show a preferred surface-sensitive diode laser 5 for use in the present sensor 1. The sensor 1 includes a substrate 3 having a bottom surface 29 and a top surface 31. A contact layer 32 is positioned on the bottom surface 29 of the substrate 3. A surface-sensitive diode laser 5 is grown on the top surface 31 of the substrate 3. A detector 7 is positioned proximate the diode laser 5 or included in the internal structure of the diode laser 5. The diode laser 5 further includes a lasing structure 33 positioned on the top surface 31 of the substrate 3 and a cap layer 15 positioned on the lasing structure 33. A segmented electrode 35 is positioned on the cap layer 15. The segmented electrode 35 includes a first electrode 37 and a second electrode 38 separated by a surface-sensitive region 11. The surface-sensitive region 11 further includes a sensitive coating 9 prepared on the cap layer 15 in the surfacesensitive region 11. A bonding layer 19 for covalently bonding the coating 9 to the cap layer 15 is also provided. The bonding layer 19 is preferably an oxide layer. The lasing structure 33 of the diode laser 5 includes a lower laser region 39 positioned on the top surface 31 of the substrate 3, an upper laser region 41 and a quantum well 43 sandwiched between the upper laser region 41 and the lower laser region 39. The lower laser region 39 includes a n-clad layer 45 positioned on the top surface 31 of the substrate 3 and an n-guide layer 47 overlying the n-clad layer 45. The upper laser region 41 includes a p-guide layer 49 positioned on the quantum well 43 and a p-clad layer 51 overlying the p-guide layer 49. The cladding and guide layers are preferably aluminum gallium arsenide layers. The quantum well 43 preferably includes a central layer 53 sandwiched between a pair of undoped layers 55, 57. The central layer 53 is preferably a gallium indium phosphide well and the undoped layers 55, 57 are preferably gallium arsenide layers. In preferred embodiments of the present sensor 1, a p-layer 59 is positioned between the cap layer 15 and the lasing structure 33. Preferably, the cap layer 15 is a gallium arsenide layer having p-conductivity. The first 37 and second 38 electrodes are gold electrodes and the first contact layer 32 is a n-type Ge/Au/Ni contact layer. The substrate 3 is a doped n-type gallium arsenide substrate.

The sensor 1, including the diode laser 5, may have any acceptable dimensions. In one preferred embodiment, the sensor diode laser/substrate combination has a length of approximately 1000 μm and a width of approximately 500 μm. The electrodes 37, 38 preferably extend across the cap layer 15 of the diode laser 5 from its side edges and preferably have widths of about 100 μm. The surface-sensitive region 11 defined by the electrodes 37, 38 is preferably about 150 μm in length and 100 μm in width. The cap layer thickness in the surface-sensitive region 11 is preferably approximately 100–200 nm. The thickness of the native oxide bonding layer 19 is preferably about 3 nm.

In one preferred embodiment of the present invention 1, the layers of the diode laser 5 have approximately the following thicknesses: n-clad layer 45, 1400 nm; n-guide 47, 200 nm, quantum well region 43, 22 nm, with the undoped layers 55, 57 being approximately 7 nm each and the central layer 53 being approximately 8 nm; p-guide 49, 200 nm, p-clad layer 51, 250 nm; p-type layer 59 positioned on the p-clad layer 51, 25 nm; and the cap layer 15, 100 nm in the current-pumped regions, and 100–200 nm in the surface-sensitive region 11.

In preferred embodiments of the present sensor 1, the surface-sensitive region 11 has a thick absorbing film coating 9 of approximately 10 nm deposited on an oxide layer that is grown on a p-GaAs cap layer.

The sensitivity of the diode laser sensor 1 is increased through the use of a saturable absorbing coatings 9 in the surface sensitive region 11 as an indicator of the presence of receptor-ligand reactions. Deposition of micron thick coatings with immobilized absorbing dyes of surface-sensitive diode lasers results in an increase of as much as 80% in the laser threshold current. Partial removal of the absorbing dye from the diode laser surface results in partial reduction of the diode laser threshold current.

Saturable absorption in dyes occurs when the number of dye molecules in the ground state is reduced by excitation either to the first singlet state by optical pumping or to the lowest triplet state by intersystem crossing. Depopulation of the dye molecule ground state results in saturation of the absorption of the dye and the dye is said to be "bleached". When a diode laser operates with a saturable absorber in the surface-sensitive region, small changes in the amount of absorber present affects the intensity of the light in the vicinity of the saturable absorber which, in turn, affects the absorption coefficient of the dye and the mode loss coefficients of the diode laser. Selection of suitable operational conditions increases the magnitude of that effect. In a competitive binding assay, the addition of the unlabeled antigen reduces the losses of the diode laser, allowing the laser to emit coherent light. The amplitude of the coherent emission is amplified to provide sensitivity which matches or exceeds that available by fluorescence assay.

In the present diode laser-based biosensors, suitable absorbent or fluorescent materials to serve as labels for immunological or nucleic acid binding events are included in the responsive coating. Preferable fluorescent labels include some or all of the following characteristics: high quantum yield, large Stoke's shift, accessibility of excitation maxima to inexpensive light sources, chemical and photochemical stability, low susceptibility to fluorescence quenching and the presence of reactive functional groups. When the present surface-sensitive diode laser is used in conjunction with near-IR dyes to label an immunochemical structure, most interference from environmental molecules is eliminated. The selection of the appropriate excitation wavelength must take into account the presence of high order vibrational overtones within the range of excitation wavelengths as well as the absorption and fluorescence of biological matrix molecules and solvents that may interfere with detection. Confinement of the excitation energy to the evanescent field above the diode laser further reduces the effects of absorption from unbound interfering molecules. In one preferred embodiment, the label is a dye having an absorption coefficient of $10^7$ $m^{-1}$ or greater and the excitation wavelength is between 920 and 960 nm, inclusive.

Figure 5:
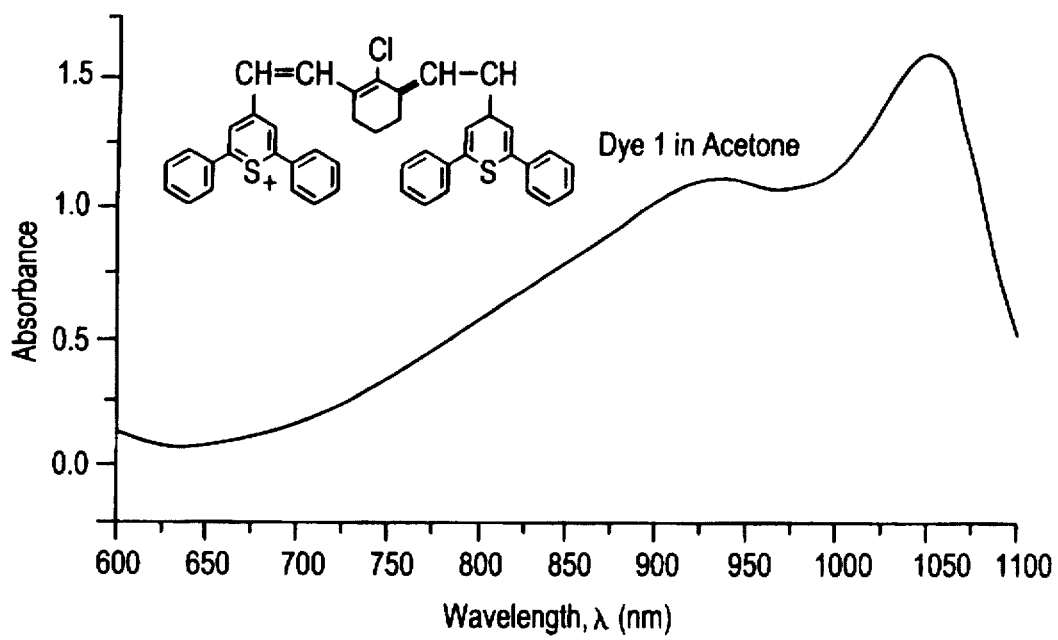
FIG. 5 graphically shows the absorption spectrum of dye 4(2-(2-chloro-3-((2,6 diphenyl-4H-thiopyran-4-ylidene) ethylidene)1-cyclohexen-1-yl)ethenyl)-2,6-diphenylthiopyrylium tetrafluoroborate (Aldrich 40,512-4) in acetone.
Figure 6:
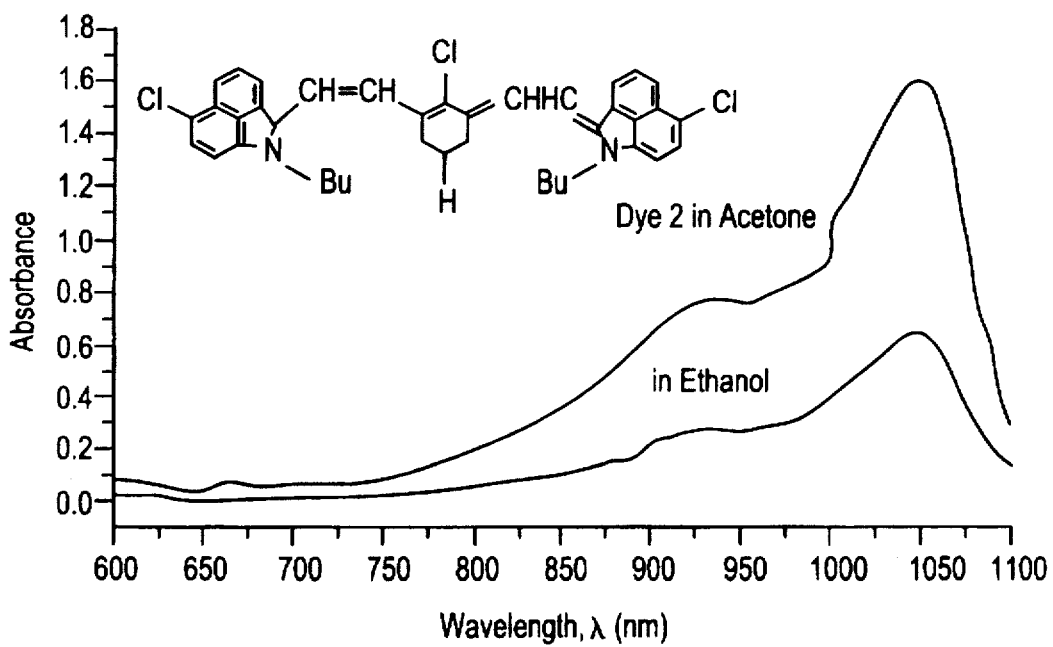
FIG. 6 graphically shows the absorption spectra of dye 1-Butyl-2-(2-(3-((1-butyl-6-clorobenz(cd)indol-2(1H)-ylidene)ethylidene)-2-chloro-1-cyclohexen-1-yl)ethenyl)-6-chlorobenz(cd) indolium tetrafluorborate (Aldrich 40,517-5) in ethanol and in acetone.

In preferred embodiments of the present sensor for use in chemical sensing applications, the label coating applied to the diode laser sensor surface includes a dye having considerable absorption in the near-IR wavelength range. In one embodiment, the label coating is a polymer coating including the dye 4-(2-(2-chloro-3-((2,6 diphenyl-4H-thiopyran-4-ylidene)ethylidene)-1-cyclohexen-1-yl)ethenyl)-2,6-diphenylthiopyrylium tetrafluoroborate (Aldrich 40,512-4). In another preferred embodiment, the label coating is a polymer coating including the dye 1-Butyl-2-(2-(3-((1-butyl-6-clorobenz(cd)indol-2(1H)-ylidene)ethylidene)-2-chloro-1-cyclohexen-1-yl)ethenyl)-6-chlorobenz(cd) indolium tetrafluorborate (Aldrich 40,517-5). As shown in FIGS. 5 and 6, both dyes exhibit substantial absorption in the 940 nm to 960 nm wavelength range. The dyes are preferably immobilized in a Nafion binder.

Figure 7:
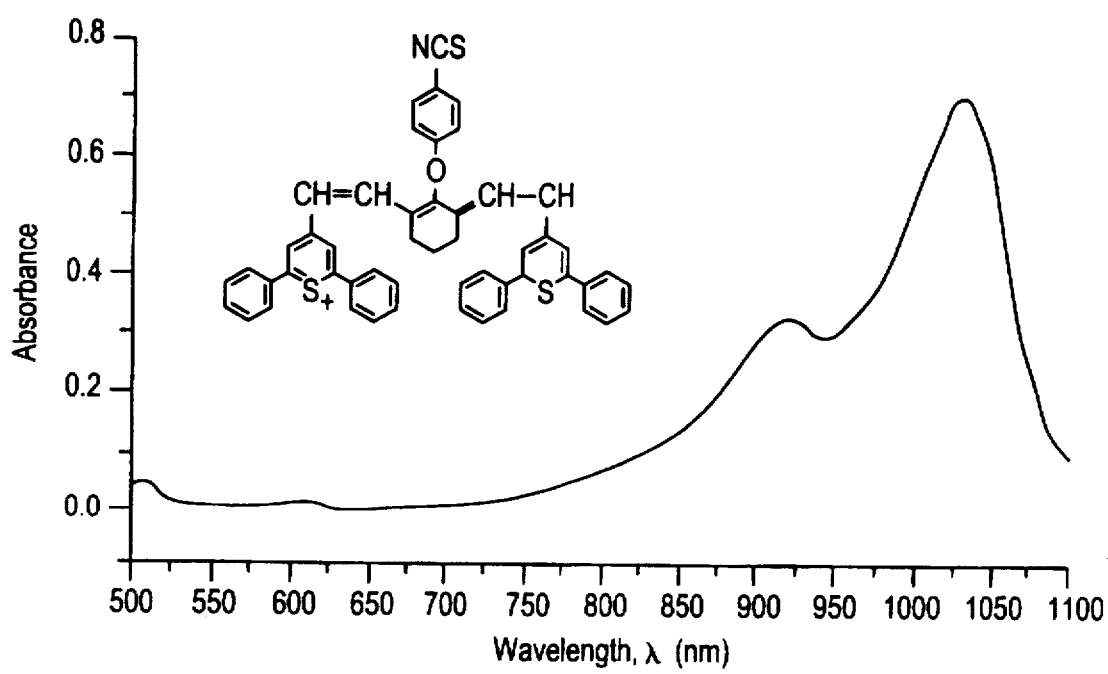
FIG. 7 graphically shows the absorption spectrum of dye 4-(2-(2-chloro-3-((2,6 diphenyl-4H-thiopyran-4-ylidene) ethylidene)-1-cyclohexen-1-yl)ethenyl)-2,6-diphenylthiopyrylium tetrafluoroborate (Aldrich 40,512-4) with pendant isocyanato functional group.

In other preferred embodiments, fluorescent dyes exhibiting considerable absorption when excited at about 940 nm to 960 nm are synthesized with pendant isothiocyanate function groups for use as a coating material. In one preferred embodiment, the label coating includes the dye 4-(2-(2-chloro-3-((2,6 diphenyl-4H-thiopyran-4-ylidene) ethylidene)-1-cyclohexen-1-yl)ethenyl)-2,6 diphenylthiopyrylium tetrafluoroborate (Aldrich 40,512-4) having an attached pendant isothiocyanato functional group. The absorption characteristics of the dye-isothiocyanate coating are shown in FIG. 7. Many other polymer-dye combinations are possible. For example, napthalocyanine dyes having Vanadium metal centers may be used for chemical detection. Those dyes demonstrate near-infrared absorption maxima in the 800 nm to 900 nm range. Further optimization of the absorption wavelength is achieved by adding electron donating functionalities to the naphthalene structure. If longer wavelengths are required anthracocyanines are synthesized following similar chemistries. Naphthalocyanine dyes are advantageous in exhibiting extreme chemical and light stability, thereby providing a label with increased shelf-life and reduced degradation during sensor operation. Generally, naphthalocyanine dyes have greater stabilities than carbocyanine dyes under similar operating conditions.

Preferably, the dyes exhibit little or no photodegradation when illuminated in the evanescent field of the diode laser.

In other preferred embodiments of the present sensor, a coating 9 of non-absorbing materials is coupled to the surface of the sensor 1. In one preferred embodiment, the coating 9 includes antibody materials to which biological materials in the sensing environment adhere. In another preferred embodiment, the coating 9 includes nucleic acid materials of a known sequence.

Selection of covalent coupling material layer 19 greatly affects the thickness of the capture antibody and labeled antigen probe layers 9 which, in turn affects the sensitivity of the diode laser sensor 1. In preferred embodiments, a thiol-containing coupling material is used to provide reduced distance between probe materials and the diode laser surface. When GaAs cap layers are used, mercaptosilane coupling materials, such as 11-mercaptoundecanoic acid, may be used. Also, carbodiimide coupling agents work successfully to bond proteins to GaAs surfaces through interaction with 11-mercaptoundecanoic acid.

Further increases in the sensitivity of diode laser-based biosensors is observed as a result of the rapid decay of the evanescent field in the surface-sensitive region with increasing distance from the surface of the sensor. Total internal reflection techniques are used to improve sensitivity. One preferred means for providing total internal reflection is to passivate the end facets of the diode laser of the present sensor. Another acceptable total internal reflection means includes etching a Bragg reflector grating in the cap layer of the diode laser beneath the electrodes. The grating should not extend in the surface-sensitive region.

Total internal reflection is the phenomenon occurring when light originating in an optically dense region with a refractive index, $n_i$, impinges on a boundary separating the dense medium from a less-dense medium with refractive index, $n_r$. For a small angle between the incident light and the normal to the interface, a certain amount of light is transmitted and the remainder is reflected. As the incidence angle, $\theta$, exceeds a critical value, $\theta_c$, given by Snell's law, $\theta_c = \sin^{-1}(n_r/n_i)$, the magnitude of the transmitted beam decreases to zero, and all of the light is internally reflected. The critical angle is decreased by increasing the refractive index difference between the base material and waveguide. In total internal reflection, the excitation intensity, I, of the evanescent wave varies with distance from the interface in the less-dense medium as the inverse exponential of the distance, x, over a characteristic depth, d, as follows:

$$I(x) \propto I_o e^{-x/d}$$

where $I_o$ is the light intensity at the surface. The penetration depth, d, of the evanescent field is controlled by the excitation wavelength, $\lambda_o$, the refractive indices of the media and the angle of incidence, $\theta$, according to the equation $$d = (\lambda_o/2\pi)[n_i^2 \sin^2 \theta - n_r^2]^{-1/2}.$$

The maximum depth of penetration is reached as the angle of incidence approaches the critical angle, where the depth of penetration is infinite. The characteristic of total internal reflection is particularly attractive for biologically selective sensor applications where the sensitivity of the biosensor depends on the ability to distinguish bound probe molecules from those present in solution.

Further improvements in laser stability are achieved by passivating the cap layer through deposition of thin organic or inorganic films at the laser surface.

The present sensor includes means for detecting the optical output of the diode laser or changes in diode laser electrical characteristics. In one preferred embodiment of the present sensor, spectral techniques are used to monitor the diode laser's output characteristics. The detecting means preferably includes a wavelength sensitive detector such as a grating-based spectrograph, a Fizeau interferometer, a Fourier transform interferometer or any other wavelength sensitive interferometer. Preferably, the detecting means includes a grating in combination with an array detector, such as a charged coupled device camera or a photodiode array.

In other preferred embodiments of the present sensor, detecting means for monitoring changes in electrical characteristics, such as output power-injection current characteristics, is provided. The detecting means preferably includes a pulse generator for developing a current pulse for use with the diode laser, a micropositioner, a photodiode and gated electronics. The pulse generator delivers a desired current pulse at a constant repetition rate to the diode laser through a micropositioner. The photodiode receives the emitted laser signal and converts the laser signal to an electrical signal. The current of the electrical signal is compared to the current signal from the pulse generator using the gated electronics for detecting and identifying chemicals.

An extremely sensitive diode laser sensor is developed using a wavelength-sensitive detector. Changes in center wavelength and the spectral width of the emission peak of the diode laser is used to monitor the thin film deposition process. The threshold and operating characteristics of the diode laser are dependent upon probe thickness, refractive index and losses through a relationship involving the overlap between the active mode fields of the laser and the quantum well electron-hole pair regeneration region. The surface-sensitive diode laser with wavelength-sensitive detection is capable of detecting the deposition of a 1.5 nm thick dielectric layer on the waveguide surface.

Figure 8:
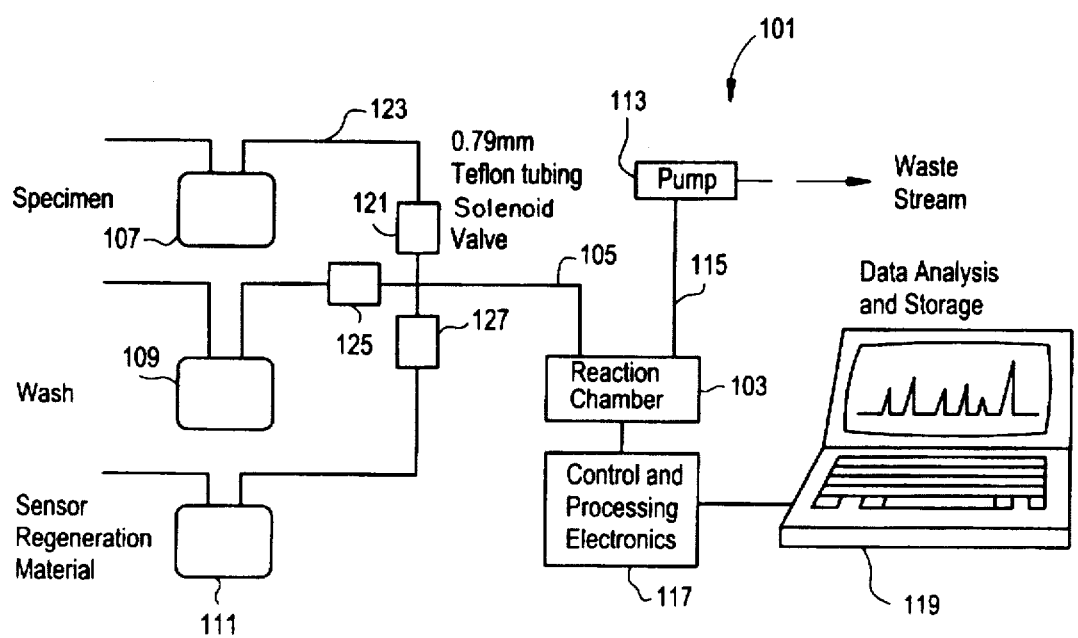
FIG. 8 schematically shows a biosensor instrument system including a diode laser biosensor and flow injector for sample transport.

FIG. 8 shows a biosensor instrument system that includes the present surface-sensitive diode laser-based sensor 1. The system includes a reaction chamber 103 or flow cell. The present sensor 1 is housed in the chamber 103. A supply line 105 delivers a selected flow from one of the following sources: a specimen source 107, a wash source 109 or a sensor regeneration material source 111. A pump 113 is connected to the chamber 103 by an effluent line 115 for moving the flow through the chamber 103. Control and processing electronics 117 are connected to the diode laser sensor 1 for monitoring the surface-sensitive effects resulting from the specimen flow. The control and processing electronics 117 may be connected to a computer 119 for data analysis and storage.

To operate the system 101, the present sensor 1 is enclosed within the reaction chamber 103. The solenoid valve 121 in the feed line 123 from the specimen source 107 is opened, allowing a specimen flow to enter the influent line 105 leading to the reaction chamber 103. The specimen flow is pulled through the chamber 103 via the pump 113 positioned in the effluent line 115. The specimen flow passes over and reacts with the surface-sensitive region of the sensor 1, resulting in detectable effects in the output of the diode laser or changes in the diode laser's electrical characteristics. Those effects are monitored by the control and processing electronics 117 and analyzed and store in a personal computer 119. Once an adequate sample has been delivered to the chamber 103, valve 121 is closed and the wash valve 125 is opened. A wash flow for clearing all remaining specimen from the chamber and for cleaning the sensor 1 passes through the chamber 103. Once adequately cleaned, valve 125 is closed-and the regeneration valve 127 is opened, allowing sensor regeneration material to pass through the chamber 103. By supplying the regeneration material, the sensor 1 returns to its original condition and is available for subsequent monitoring applications. By regenerating the biosensor surface, reduced costs per sample are obtained.

While the invention has been described with reference to specific embodiments, modifications and variations of the invention may be constructed without departing from the scope of the invention, which is defined in the following claims.

We claim:

1. A surface-sensitive diode laser sensor apparatus comprising a substrate having a bottom surface and a top surface, a diode laser grown on the top surface of the substrate, and a detector positioned proximate the diode laser or included in an internal structure of the diode laser, wherein the diode laser further comprises a lasing structure positioned on the top surface of the substrate, a cap layer positioned on the lasing structure, a segmented electrode positioned on the cap layer, wherein the segmented electrode further comprises a first electrode and a second electrode separated by a surface-sensitive region, and wherein the surface-sensitive region further comprises a sensitive coating prepared on the cap layer in the surface-sensitive region.

2. The apparatus of claim 1, wherein the lasing structure further comprises a lower laser region positioned on the upper surface of the substrate, an upper laser region and a quantum well sandwiched between the upper laser region and the lower laser region.

3. The apparatus of claim 2, wherein the lower laser region further comprises an n-cladding layer positioned on the upper surface of the substrate and an n-guide layer overlying the n-cladding layer, and wherein the upper laser region further comprises a p-guide layer positioned on the quantum well and a p-cladding layer overlying the p-guide layer.

4. The apparatus of claim 3, wherein the cladding and guide layers are aluminum gallium arsenide layers.

5. The apparatus of claim 2, wherein the quantum well further comprises a central layer sandwiched between a pair of undoped GaAs layers.

6. The apparatus of claim 5, wherein the central layer comprises gallium indium phosphide and wherein the undoped layers are gallium arsenide layers.

7. The apparatus of claim 1, further comprising a p-layer positioned between the cap layer and the lasing structure.

8. The apparatus of claim 1, wherein the cap layer is a gallium arsenide layer having p-conductivity.

9. The apparatus of claim 1, wherein the first and second electrodes are gold electrodes.

10. The apparatus of claim 1, further comprising a contact layer positioned on the bottom surface of the substrate and wherein the contact layer is a n-type Ge/Au/Ni contact layer.

11. The apparatus of claim 1, wherein the substrate is a doped n-type gallium arsenide substrate.

12. The apparatus of claim 1, wherein end facets are defined by side edges of the diode laser, and further comprising an inorganic chemical coating applied to the end facets for passivating the end facets.

13. The apparatus of claim 1, wherein upper surface of the cap layer outside of the surface sensitive region further comprises a grating surface having surface corrugations.

14. The apparatus of claim 13, wherein the grating surface further comprises Bragg grating reflectors.

15. The apparatus of claim 1, further comprising a coupling layer positioned between the sensitive coating and the cap layer.

16. The apparatus of claim 15, wherein the coupling layer is an oxide layer.

17. The apparatus of claim 1, wherein the sensitive coating further comprises an absorbing dye or a fluorescent dye immobilized in a polymer or ceramic material.

18. The apparatus of claim 17, wherein the dye is selected from the group consisting of 4-(2-(2-chloro-3-((2,6 diphenyl-4H-thiopyran-4-ylidene)ethylidene)-1-cyclohexen-1-yl)ethenyl)-2,6 diphenylthiopyrylium tetrafluoroborate in a Nafion binder, 1-Butyl-2-(2-(3-((1-butyl-6-clorobenz(cd)indol-2(1H)-ylidene)ethylidene)-2-chloro-1-cyclohexen-1-yl)ethenyl)-6-chlorobenz(cd) indolium tetrafluorborate in a Nafion binder, 4-(2-(2-chloro-3-((2,6 diphenyl-4H-thiopyran-4-ylidene)ethylidene)-1-cyclohexen-1-yl)ethenyl)-2,6 diphenylthiopyrylium tetrafluoroborate having an attached pendant isothiocyanato functional group, 1-Butyl-2(2-(3-((1-butyl-6-clorobenz(cd) indol-2(1H)-ylidene)ethylidene)-2-chloro-1-cyclohexen-1-yl)ethenyl)-6-chlorobenz(cd) indolium tetrafluorborate having an attached pendant isothiocyanato functional group, napthalocyanine dyes, and napthalocyanine dyes having Vanadium metal centers.

19. The apparatus of claim 1, wherein the sensitive coating further comprises non-absorbing materials selected from the group consisting of antibody materials and nucleic acid materials of a known sequence.

20. The apparatus of claim 1, wherein the detector is a wavelength-sensitive detector for measuring an optical output of the lasing structure.

21. The apparatus of claim 20, wherein the wavelength-sensitive detector is selected from the group consisting of grating-based spectrograph, a Fizeau interferometer, a Fourier transform interferometer or any other wavelength sensitive interferometer, and a grating in combination with an array detector.

22. The apparatus of claim 1, wherein the detector monitors changes in electrical characteristics.

23. The apparatus of claim 22, wherein the detector further comprises a pulse generator for developing pulse signals at a constant repetition rate and for delivering the pulse signals through a micropositioner to the lasing structure of the diode laser, a photodiode for receiving emitted laser signals from the lasing structure and for converting the laser signals to electrical signals, and gated electronics for comparing the electrical signals to the pulse signals from the pulse generator for detecting and identifying chemicals.

24. An optical sensor apparatus comprising a substrate having a top surface and a bottom surface, at least two diode lasers grown on the top surface of the substrate, wherein at least one of the diode lasers is a sampling laser and wherein at least one of the lasers is a referencing laser, and a detector for detecting outputs from the lasers, wherein each diode laser further comprises an n-clad layer positioned on the top surface of the substrate, a first guide layer overlying the n-clad layer, a quantum well overlying the first guide layer, a second guide layer overlying the quantum well, a p-clad layer overlying the second guide layer, a cap layer positioned on the p-clad layer and a segmented electrode positioned on the cap layer, wherein the segmented electrode further comprises a first electrode and a second electrode separated by a surface-sensitive region, wherein the surface-sensitive region further comprises a sensitive coating prepared on the cap layer in the surface-sensitive region, wherein the thickness of the cap layer of the at least one sampling laser in the surface-sensitive region is optimal for surface sensitivity, and further comprising a blocking layer positioned on the cap layer of the at least one referencing laser for removing referencing laser sensitivity.

25. The apparatus of claim 24, wherein upper surfaces of the cap layers of the diode lasers outside of the surface-sensitive regions have surface corrugations.

26. The apparatus of claim 24, wherein each diode laser has a laser generation region positioned beneath the electrodes and a laser detection region positioned at a far end of the laser, wherein the cap layer of each diode laser is discontinuous between the laser detection region and the laser generation region, and further comprising electrodes positioned on the cap layers overlying the laser detection region of the diode lasers for detecting and monitoring laser output.

27. A method for detecting trace levels of gases, biological compounds or biochemical materials in solution or in air comprising the steps of providing a surface-sensitive diode laser sensor, exposing a surface-sensitive region of the sensor to an environment including analytes of interest, and monitoring changes in optical characteristics of the diode laser sensor, wherein the sensor further comprises a substrate having a bottom surface and a top surface, a diode laser grown on the top surface of the substrate, and a detector positioned proximate the diode laser or included in an internal structure of the diode laser, wherein the diode laser further comprises a lasing structure positioned on the top surface of the substrate, a cap layer positioned on the lasing structure, a segmented electrode positioned on the cap layer, wherein the segmented electrode further comprises a first electrode and a second electrode separated by a surface-sensitive region, and wherein the surface-sensitive region further comprises a sensitive coating prepared on the cap layer in the surface-sensitive region.

28. The method of claim 27, wherein the providing step further comprises placing the sensor in a flow cell or chamber, and wherein the exposing step further comprises the step of introducing a flow carrying the analytes of interest into the flow cell or chamber.

29. The method of claim 28, further comprising the steps of delivering a washing flow to the chamber following the monitoring step, removing the washing flow from the chamber and regenerating the sensor without removing the sensor from the chamber, the regenerating step further comprising delivering a flow of sensor regeneration materials to the chamber.

30. The method of claim 27, wherein the sensitive coating further comprises materials selected from the group consisting of absorbing dyes, fluorescent dyes, and non-absorbing materials selected from the group consisting of antibody materials and nucleic acid materials of a known sequence.

31. The method of claim 27, wherein the sensor further comprises multiple diode lasers having surface-sensitive regions deposited on the substrate, and further comprising the step of rendering at least one, but less than all, of the diode lasers insensitive to environmental conditions.

32. The method of claim 31, wherein the rendering step further comprises blocking the surface-sensitive region of the lasers.

33. A biosensor instrument system comprising a surface-sensitive diode laser-based sensor positioned in a flow cell, a supply line connected to the inlet side of the flow cell, a specimen source connected to the supply line, a wash source connected to the supply line, a sensor regeneration material source connected to the supply line, an effluent line extending from the exit side of the chamber, a pump positioned in the effluent line, and control and processing electronics electrically connected to the diode laser sensor for monitoring the surface-sensitive effects resulting from specimen flow, wherein the sensor further comprises a substrate having a bottom surface and a top surface, a diode laser grown on the top surface of the substrate, and a detector positioned proximate the diode laser or included in an internal structure of the diode laser, wherein the diode laser further comprises a lasing structure positioned on the top surface of the substrate, a cap layer positioned on the lasing structure, a segmented electrode positioned on the cap layer, wherein the segmented electrode further comprises a first electrode and a second electrode separated by a surface-sensitive region, and wherein the surface-sensitive region further comprises a sensitive coating prepared on the cap layer in the surface-sensitive region.

* * * * *